US010709426B2

(12) United States Patent
Uno et al.

(10) Patent No.: US 10,709,426 B2
(45) Date of Patent: Jul. 14, 2020

(54) ULTRASONIC DIAGNOSTIC SYSTEM

(71) Applicant: Hitachi, Ltd., Tokyo (JP)

(72) Inventors: Takaya Uno, Tokyo (JP); Taro Eguchi, Tokyo (JP); Takuya Kitamaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 446 days.

(21) Appl. No.: 15/547,209

(22) PCT Filed: Feb. 8, 2016

(86) PCT No.: PCT/JP2016/053620
§ 371 (c)(1),
(2) Date: Jul. 28, 2017

(87) PCT Pub. No.: WO2016/129544
PCT Pub. Date: Aug. 18, 2016

(65) Prior Publication Data
US 2018/0021025 A1    Jan. 25, 2018

(30) Foreign Application Priority Data

Feb. 10, 2015   (JP) ................................. 2015-024407

(51) Int. Cl.
*A61B 8/00* (2006.01)
*A61B 8/14* (2006.01)
*G06F 1/16* (2006.01)
*G01S 7/52* (2006.01)
*G16H 50/20* (2018.01)
(Continued)

(52) U.S. Cl.
CPC .................. *A61B 8/56* (2013.01); *A61B 8/14* (2013.01); *A61B 8/4427* (2013.01); *A61B 8/4433* (2013.01); *A61B 8/4472* (2013.01);

*A61B 8/461* (2013.01); *A61B 8/54* (2013.01); *G01S 7/52082* (2013.01); *G01S 7/52096* (2013.01); *G06F 1/1626* (2013.01); *G06F 1/1632* (2013.01); *G06F 1/1654* (2013.01); *G06F 1/1698* (2013.01); *G16H 30/40* (2018.01);
(Continued)

(58) Field of Classification Search
CPC .................................. A61B 8/56; G16H 50/20
See application file for complete search history.

(56) References Cited

FOREIGN PATENT DOCUMENTS

JP        2008-000406 A        1/2008
JP        2008-114065 A        5/2008
(Continued)

OTHER PUBLICATIONS

International Search Report received for PCT Patent Application No. PCT/JP2016/053620, dated Apr. 26, 2016, 3 pages.

*Primary Examiner* — Joseph M Santos Rodriguez
(74) *Attorney, Agent, or Firm* — Baker Botts L.L.P.

(57) ABSTRACT

In the present invention, an FE device and a BE device communicate using two wireless communication routes in a separate state. Approaching of each device is determined in both devices immediately prior to a docking state by monitoring of a wireless communication state. Wireless communication between the two devices is then stopped, and both devices enter a freeze state (operation-limited state). When the docking state is then formed, wired communication is established between both devices. Then, when an unfreeze input occurs, both devices return to a normal operation state. Both devices temporarily enter the freeze state also when a state change from the docking state to the separate state occurs.

13 Claims, 12 Drawing Sheets

(51) Int. Cl.
*G16H 40/63* (2018.01)
*G16H 30/40* (2018.01)

(52) U.S. Cl.
CPC ............. *G16H 40/63* (2018.01); *G16H 50/20* (2018.01); *A61B 8/4254* (2013.01)

(56) References Cited

FOREIGN PATENT DOCUMENTS

| | | |
|---|---|---|
| JP | 2011-005241 A | 1/2011 |
| JP | 2011-087841 A | 5/2011 |
| JP | 2014-117360 A | 6/2014 |
| WO | 2013/145825 A1 | 10/2015 |

|  | CONTENTS | DOCKING STATE | SEPARATED STATE |
|---|---|---|---|
| FIRST WIRELESS COMMUNICATION MODE | HIGH SPEED (IEEE 802.11) | STOP | IN USE |
| SECOND WIRELESS COMMUNICATION MODE | LOW SPEED/LOW POWER CONSUMPTION (IEEE 802.15.1) | STOP | IN USE |
| WIRE COMMUNICATION MODE | — | IN USE | STOP |

FIG. 6

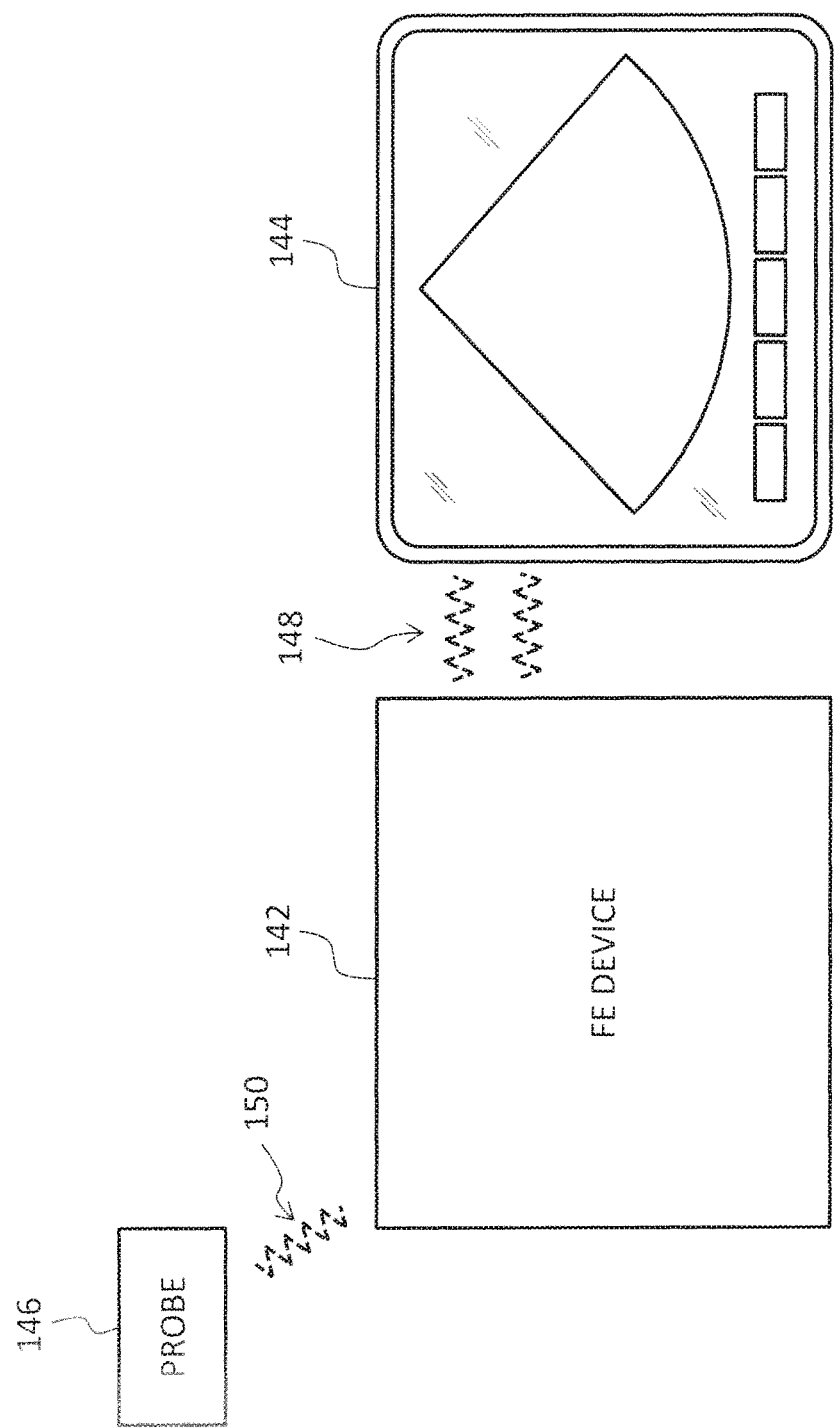

ULTRASONIC DIAGNOSTIC SYSTEM

CROSS-REFERENCE TO RELATED APPLICATIONS

This application is a national phase claiming the benefit of and priority to International Patent Application No. PCT/JP2016/053620, entitled "ULTRASONIC DIAGNOSTIC SYSTEM", filed Feb. 8, 2016, which claims priority to Japanese Patent Application No. 2015-024407, filed Feb. 10, 2015, which are hereby incorporated by reference in their entireties.

TECHNICAL FIELD

The present invention relates to an ultrasonic diagnostic system, and more particularly to an ultrasonic diagnostic system composed of a plurality of devices connected wirelessly and through wire.

BACKGROUND

Ultrasonic diagnostic systems are apparatuses that form an ultrasound image based on received signals obtained by transmitting and receiving ultrasound waves with respect to a living body. When an ultrasonic diagnostic system is composed of a plurality of independent devices (a plurality of units or modules), these devices are generally used in a separated state or in a docking state. In the separated state, the plurality of devices are connected with each other according to a wireless communication mode. In the docking state, the plurality of devices are connected with each other according to a wire communication mode. The docking state can include a state in which two devices are connected through a cable.

Patent Document 1 discloses an ultrasonic diagnostic system including a first casing and a second casing that are always coupled with each other physically. Patent Document 2 discloses an ultrasonic diagnostic system composed of a front-end device and a back-end device. These devices cannot be separated from each other and connected with each other according to a wire communication mode. Patent Document 3 discloses an ultrasonic diagnostic system including a device main body and an ultrasound probe which are connected wirelessly to preform wireless communication for transmission and wireless communication for reception between the devices. This configuration prohibits wire communication between the devices. Patent Document 4 discloses an ultrasonic diagnostic system capable of using both a wireless probe and a wire probe. Patent Document 4 does not disclose a probe adaptable for both a wireless mode and a wire mode.

CITATION LIST

Patent Literature

Patent Document 1: JP 2011-5241 A
Patent Document 2: JP 2008-114065 A
Patent Document 3: JP 2011-87841 A
Patent Document 4: JP 2008-406 A

SUMMARY

Technical Problem

For an ultrasonic diagnostic system including a plurality of individual devices that can be separated from each other, the following needs exist in accordance with diagnosis situations or the examiner's preferences: the examiner wishes to use these devices in a separated state in which the devices are physically separated from each other or in a docking state in which the devices are physically coupled with each other. Ultrasonic diagnostic systems that can satisfy both needs are expected.

In such an ultrasonic diagnostic system, it is necessary to ensure proper operations or operation stability of each device during a shift from the separated state to the docking state and a shift from the docking state to the separated state. Because a change in the state generally involves a change in data processing conditions and control conditions, it is desirable to avoid problems of unstable data processing and display of improper images. In the change of state from the separated state to the docking state, as the distance between the two units becomes shorter, saturation is more likely to occur at the time of receiving radio waves (which appears as an increased error rate, for example), which may cause a problem that proper wireless communication cannot be performed.

An advantage of the invention is to avoid an unstable or improper operation in an ultrasonic diagnostic system including a plurality of separate devices, even when a physical relationship of these devices or a communication mode among the plurality of devices is changed. An alternative advantage of the invention is to avoid any operational problems during transition of a state from a separated state to a docking state. Another alternative advantage of the invention is to provide an ultrasonic diagnostic system with good usability, for which a separated state or a docking state is selectable.

Solution to Problem

In accordance with one aspect, an ultrasonic diagnostic system includes a first device configured to function for ultrasonic diagnosis, and a second device configured to function, with the first device, for the ultrasonic diagnosis. In a separated state in which the first device and the second device are separated from each other, the first device and the second device communicate with each other according to a wireless communication mode. In a docking state in which the first device and the second device are coupled to each other, the first device and the second device communicate with each other according to a wire communication mode. The ultrasonic diagnostic system further includes an immediately-before determining unit configured to determine immediately-before state of docking during a course of a change of state from the separated state to the docking state. The first device includes a first controller configured to cause an operation state of the first device to transition from a normal operation state to an operation limited state when the immediately-before state of docking is determined. The second device includes a second controller configured to cause an operation state of the second device to transition from a normal operation state to an operation limited state when the immediately-before state of docking is determined.

The above ultrasonic diagnostic system can operate in both the separated state and the docking state. This mechanism allows selection of an appropriate usage mode in accordance with diagnosis situations, examiner's preference, and other conditions. In the course of a change of state from the separated state to the docking state, the immediately-before determining unit determines immediately-before state of docking. Based on this determination, prior to docking of the first device and the second device, each device can execute control to avoid problems associated with the change of state. Although a simple change of the communication mode at the time of docking would result in unstable synchronization and unnatural images, for example, determining the immediately-before state of docking and setting the operation state of each device to a fixed state based on the determination should be able to prevent the above problems. More specifically, the system operation can be restricted so as to avoid the problems. In general, an ultrasonic examination is not actually performed with respect to an examinee in the course of a change of state from the separated state to the docking state. It is therefore desirable to restrict the operation in consideration of this situation. For example, it is desirable that, on determining immediately-before state of docking, wireless communication is stopped and the operation of each of the first and second devices is caused to transit from a real-time operation state to a freeze state. In this state, the operation of the transmitting circuit (and the receiving circuit), for example, is stopped, and the operation of the booster circuit is also stopped. Further, moving image display is changed to still image display.

The separated state generally refers to a state in which two devices are physically or mechanically separated from each other, and the docking state generally refers to a state in which two devices are physically or mechanically coupled to each other. In the docking state, a plurality of communication lines are connected according to connector connection, which practically corresponds to cable connection. In preferred embodiments, the first device is a front-end device closer to a living body, and the second device is a back-end device distant from the living body. The first device may be formed of a probe, and the second device may be formed of an ultrasonic diagnostic device main body.

The immediately-before determining unit determines a state immediately before the docking state, and this state (immediately before the docking) is practically a state in which two devices are spatially proximate to each other. The immediately-before state of docking can be determined based on the intensity of transmission radio waves (if a distance-linked transmitting circuit is adopted), the intensity of received electric field, a received error rate, and other parameters, or determined using various sensors such as a proximity sensor. Prior to formation of the docking state, operation conditions may be switched in three or more stages, rather than in two stages.

In preferred embodiments, the first device includes a transmitting circuit, and the first controller is configured to stop operation of the transmitting circuit at the time of transition to the operation limited state. This mechanism saves power. In preferred embodiments, the first device includes a power source circuit including a booster converter, and the first controller is configured to stop operation of the booster converter at the time of transition to the operation limited state. This mechanism not only saves power but also enhances safety. In preferred embodiments, the second controller is configured to change moving image display to still image display at the time of transition to the operation limited state. This mechanism can avoid display of unnatural images, thereby preventing the examiner or the examinee from feeling uneasy.

In preferred embodiments, the immediately-before state determining unit is configured to determine the immediately-before state of docking when the first device and the second device are in a proximity relationship. In preferred embodiments, the immediately-before state determining unit is configured to determine the immediately-before state of docking based on a wireless communication state between the first device and the second device. Determination of the immediately-before state of docking using information generally obtainable in wireless communication simplifies a system configuration.

In preferred embodiments, the immediately-before state determining unit includes a first immediately-before state determining unit disposed in the first device and configured to determine the immediately-before state of docking based on the wireless communication state; and a second immediately-before state determining unit disposed in the second device and configured to determine the immediately-before state of docking based on the wireless communication state. The first controller is configured to cause the operation state of the first device to transition to the operation limited state when the first immediately-before state determining unit determines the immediately-before state of docking, and the second controller is configured to cause the operation state of the second device to transition to the operation limited state when the second immediately-before state determining unit determines the immediately-before state of docking. When the first device and the second device are in extremely proximity, wireless communication may be unstable or may fail to be established due to a phenomenon of saturation of a received signal. It is therefore desirable that each of the first device and the second device includes an immediately-before state determining unit to reliably determine the immediately-before state of docking in each device.

In preferred embodiments, the first controller and the second controller are configured to resume communication using the wire communication mode after transition to the operation limited state and formation of the docking state. The timing for resuming the operation can advanced by starting control for establishment of wire communication between the devices from when the docking state is formed. While automatic return to the normal operation state immediately after establishment of the docking state is possible, as it can be assumed that use of the system is terminated after establishment of the docking state, it is desirable that return to the normal operation state is performed after user input for confirmation.

In preferred embodiments, the system further include a separation determining unit configured to determine a change of state from the docking state to the separated state as separation. The first controller is configured to cause the operation state of the first device to transition from the normal operation state to the operation limited state when the separation is determined, and the second controller is configured to cause the operation state of the second device to transition from the normal operation state to the operation limited state when the separation is determined. This mechanism recognizes a state transition from the docking state to the separated state as separation (disconnection), which can then be used as a trigger to change the operation states of both devices to the operation limited state. In preferred embodiments, thereafter, the operation state is returned to the normal operation state upon input of confirmation by the user.

In preferred embodiments, the first device and the second device are configured to communicate with each other using a first wireless communication mode and a second wireless communication mode in the separated state. In preferred embodiments, the first wireless communication mode is a higher speed mode than the second wireless communication mode, the first device is a front-end device including a transmitting circuit and a receiving circuit, and the second device is a back-end device including an input device and a display device. The first wireless communication mode is used to transmit data from the front-end device to the back-end device, and the second wireless communication mode is used to transmit a control signal from the back-end device to the front-end device.

In preferred embodiments, the display device is configured to display a single communication establishment symbol when communication is established using both the first wireless communication mode and the second wireless communication mode. The communication establishment symbol is not displayed when communication is established using one of the first wireless communication mode and the second wireless communication mode and when neither the first wireless communication mode nor the second wireless communication mode establishes communication. When two wireless communication modes are used, in general, the system operation is not available until wireless communication using both wireless communication modes is established, and the system cannot be operated when only one of the wireless communication modes is established. The examiner normally would like to know whether or not the system can be operated and need not recognize each wireless communication state individually. Therefore, display of a single symbol (a communication indicator or a communication icon) indicating that communication is established with both of the two wireless communication modes is adequate for the examiner. The examiner rather prefers such a symbol so as to avoid confusion.

In accordance with another aspect, in a method of controlling an ultrasonic diagnostic system including a first device and a second device, the first device and the second device communicate with each other through a wireless communication mode in a separated state in which the first device and the second device are separated from each other, and the first device and the second device communicate with each other through a wire communication mode in a docking state in which the first device and the second device are coupled with each other. The method includes determining immediately-before state of docking during a course of a change of state from the separated state to the docking state; and, when the immediately-before state of docking is determined, causing operation states of the first device and the second device to transition to a freeze state. This method can be implemented by a control program which can be stored in a storage medium within the device or a portable storage medium, or can be transferred via the network.

BRIEF DESCRIPTION OF DRAWINGS

FIG. 6 shows communication modes in a docking state and communication modes in a separated state.

FIG. 15 is a conceptual view illustrating a system including a wireless probe.

DESCRIPTION OF EMBODIMENTS

Preferred embodiments of the invention will be described hereinafter with reference to the drawings.

(1) Ultrasonic Diagnostic System

Figure 1:
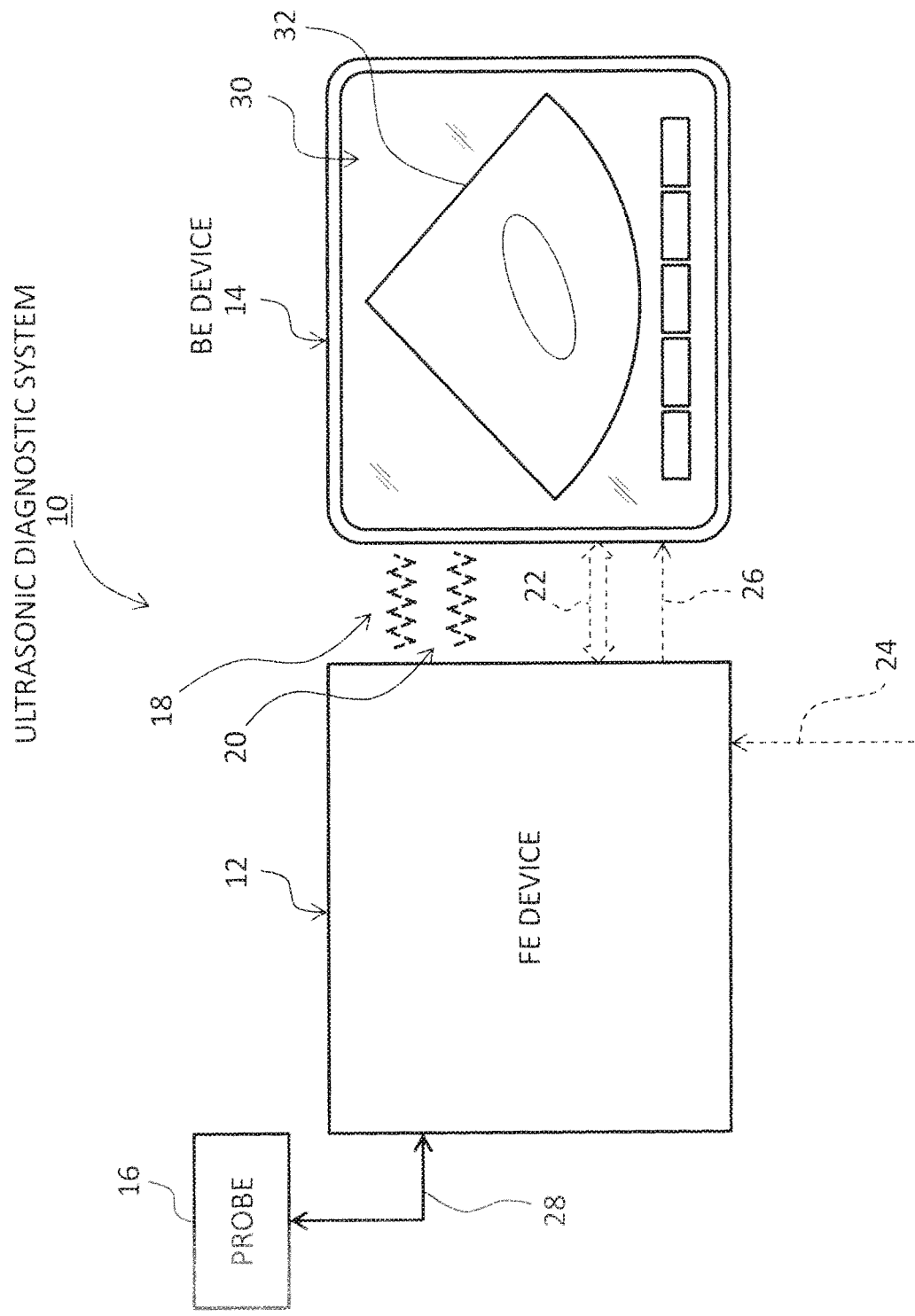
FIG. 1 is a conceptual view illustrating an ultrasonic diagnostic system according to a preferred embodiment of the invention.

FIG. 1 schematically illustrates a structure of an ultrasonic diagnostic system according to the invention. An ultrasonic diagnostic system 10 is a medical apparatus for use in medical facilities such as hospitals and is used to perform ultrasonic diagnosis with respect to an examinee (living body). The ultrasonic diagnostic system 10 is composed mainly of a front-end device (hereinafter referred to as an "FE device") 12, a back-end device (hereinafter referred to as a "BE device) 14, and a probe 16. The FE device 12 is closer to a living body than the BE device 14 and the BE device 14 is more distant from the living body than the FE device is. The FE device 12 and the BE device 14 are discrete devices, each forming a portable device. The FE device 12 and the BE device 14 can operate in a separated state in which the devices are separated from each other and can also operate in a docking state in which these devices are coupled with each other. FIG. 1 shows the separated state.

The probe 16 is a transmitter/receiver designed for transmitting and receiving ultrasound waves in contact with a surface of a living body. The probe 16 includes a 1D array transducer formed of a plurality of transducer elements arranged in a linear or arc shape. The array transducer forms ultrasound beams, which are electronically scanned repeatedly. For each electronic scanning, a beam scanning plane is formed within the living body. Known electronic scanning methods include, for example, an electronic linear scanning method and an electronic sector scanning method. In place of a 1D array transducer, a 2D array transducer capable of forming a three-dimensional echo data capturing space can be provided. In an example structure illustrated in FIG. 1, the probe 16 is connected to the FE device 12 via a cable 28. The probe 16 may be connected to the FE device 12 through wireless communication. In this case, a wireless probe is used. The probe 16 which is to be actually used may be selected from among a plurality of probes connected to the FE device 12. The probe 16 which is to be inserted into a body cavity may be connected to the FE device 12.

The FE device 12 and the BE device 14 are electrically connected to each other according to a wireless communication mode in the separated state illustrated in FIG. 1. In the present embodiment, these devices are connected to each other according to a first wireless communication mode and a second wireless communication mode. FIG. 1 clearly shows a wireless communication path 18 according to the first wireless communication mode and a wireless communication path 20 according to the second wireless communication mode. The first wireless communication mode is a higher speed mode than the second wireless communication mode, and is used in the present embodiment to transmit ultrasound received data from the FE device 12 to the BE device 14. In other words, the first wireless communication mode is used for data transmission. The second wireless communication mode is a mode of lower speed and simpler communication than the first wireless transmission mode and is used in the present embodiment to transmit a control signal from the BE device 14 to the FE device 12. In other words, the second wireless communication mode is used for control.

In the docking state in which the FE device 12 and the BE device 14 are physically coupled with each other, the FE device 12 and the BE device 14 are electrically connected with each other according to the wire communication mode. When compared to the above two wireless communication modes, the wire communication has a much higher speed. FIG. 1 illustrates a wire communication path 22 between the two devices. A power source line 26 supplies direct current power from the FE device 12 to the BE device 14 in the docking state. The power is used for operating the BE device 14 and used for charging a battery within the BE device 14.

Reference numeral 24 denotes a receiving line for DC power supplied from an AC adaptor (AC/DC converter). The AC adaptor is connected to the FE device 12 as required. The FE device 12, which also includes a built-in battery, can be operated using the battery as a power source. The FE device 12 has a box shape as will be described below. The structure and operation of the FE device 12 will be detailed below.

The BE device 14 has a tablet form or a flat board shape in the present embodiment, and basically has a structure similar to the structure of a general tablet computer. The BE device 14, however, includes various kinds of software dedicated to ultrasonic diagnosis installed therein, including an operation control program, an image processing program, and other programs. The BE device 14 includes a display panel 30 with a touch sensor, which functions as a user interface serving both as an input device and a display device. In FIG. 1, the display panel 30 indicates a B-mode tomographic image as an ultrasound image. A user enters various inputs using icons indicated on the display panel 30. A sliding operation and an enlarging operation can also be performed on the display panel 30.

In accordance with the purpose of diagnosis, preferences of the examiner, and other conditions, the ultrasonic diagnostic system 10 can be operated with a usage mode selected from the separated state and the docking state. Consequently, an ultrasonic diagnostic system with improved usability can be provided.

In order to avoid the ultrasonic diagnostic system 10 from operating unstably or improperly during a change of state, in the present embodiment, control is executed to forcibly place the ultrasonic diagnostic system 10 in a freeze state prior to the change of state. Specifically, in the course of a transition from the separated state to the docking state, immediately-before state of docking is determined in each of the FE device 12 and the BE device 14 based on the intensity of radio waves indicating a distance between the devices or a receiving state, and, based on the determination, control is executed to cause the operation state of each of the devices 12 and 14 to transition to the freeze state. After formation of the docking state and an unfreezing operation by the examiner, the freeze states of these devices 12 and 14 are actually cancelled. In the course of a transition from the docking state to the separated state, the separated state is detected individually in the FE device 12 and the BE device 14 using detection of disconnection and other methods, and then these devices 12 and 14 are placed in the freeze state. Then, after the unfreezing operation, the freeze states of the devices 12 and 14 are actually cancelled.

The BE device 14 may also be connected to a hospital LAN using a wireless communication mode and a wire communication mode. Communication paths for these modes are not shown in the drawings. The BE device 14 (or the FE device 12) may also be connected to other dedicated devices which function for ultrasonic diagnosis (e.g., a remote controller) according to the wireless communication mode or the wire communication mode.

Figure 2:
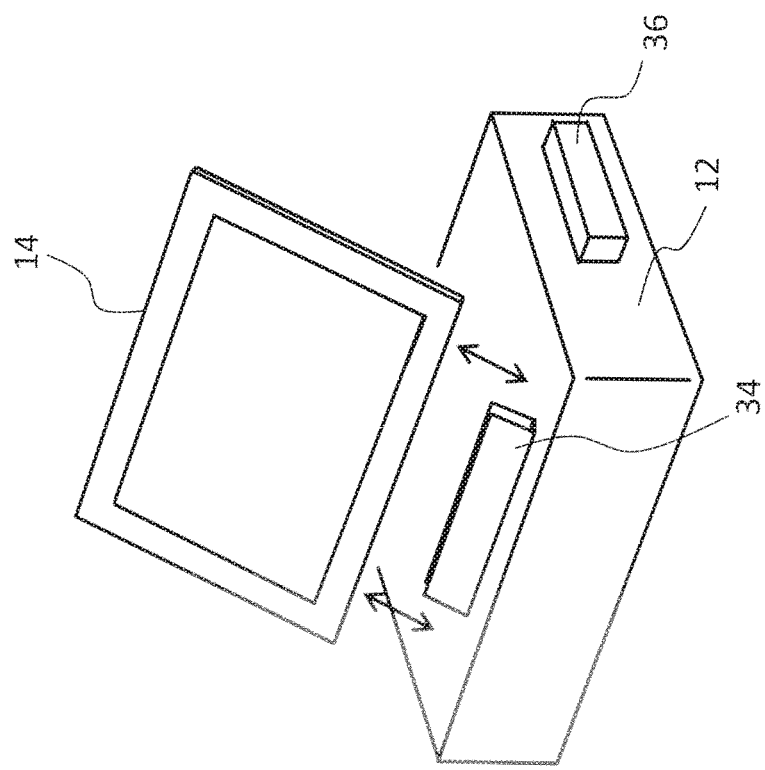
FIG. 2 is a perspective view of an ultrasonic diagnostic system in a separated state.

FIG. 2 illustrates the separated state. The FE device 12 is placed on a desk, for example. The FE device 12 includes a holder 34 having an insertion opening (slot). The holder 34 has a hinged mechanism and is pivotable about a horizontal axis. The FE device 12 includes a predetermined side surface on which a connector disposed on an end portion of a probe cable is mounted. The FE device 12 may have a chamber formed therein for accommodating a probe and other components. Such a structure is convenient for transportation of the ultrasonic diagnostic system and can also protect the probe. In FIG. 2, the BE device 14 is separated from the FE device 12. The BE device 14 can be further distant from the FE device 12, as long as wireless communication is available between the FE device 12 and the BE device 14.

Figure 3:
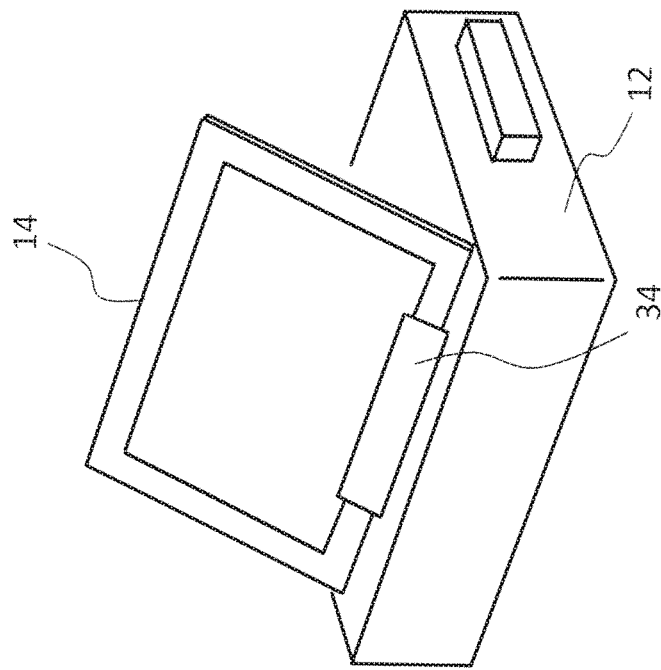
FIG. 3 is a perspective view of an ultrasonic diagnostic system in a docking state.

FIG. 3 illustrates the docking state. A lower end of the BE device 14 is inserted in the insertion opening of the holder 34. In this inserted state, wire connection is established between the FE device 12 and the BE device 14. More specifically, the devices are connected with each other via wire LAN and are also connected with each other with a wire power source line. In the docking state, an inclination angle of the BE device 14 can be varied as desired to alter the position of the BE device 14. The BE device 14 can be tilted completely on the back surface side thereof (on the top surface of the FE device 12) to obtain a horizontally flat position.

(2) Front-End Device

Figure 4:
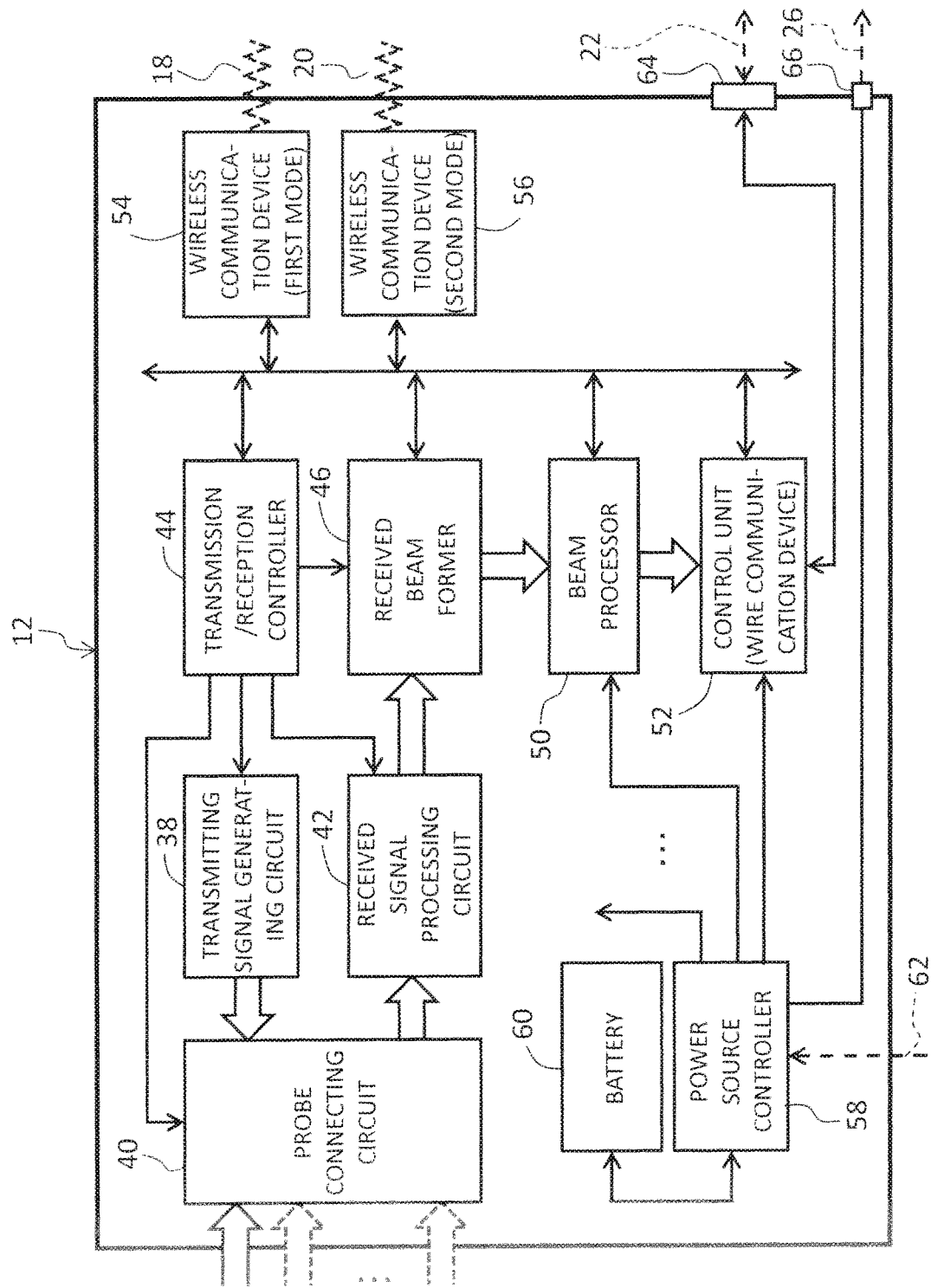
FIG. 4 is a block diagram of a front-end device.

FIG. 4 is a block diagram of the FE device 12. Individual blocks in the drawing are formed by hardware such as processors and electronic circuits. A transmitting signal generating circuit 38 supplies a plurality of transmitting signals to a plurality of transducer elements within the probe in parallel, via a probe connecting circuit 40. Upon receiving the signals, the probe forms a transmitting beam. A plurality of transducer elements, receiving reflected waves from within a living body, output a plurality of received signals, which are then input to a received signal processing circuit 42 via the probe connecting circuit 40. The received signal processing circuit 42 includes a plurality of preamplifiers, a plurality of amplifiers, a plurality of A/D converts, and other components. A plurality of digital received signals output from the received signal processing circuit 42 are fed to a received beam former 46. The received beam former 46 applies phase alignment and summation processing to the plurality of digital received signals and outputs beam data as a signal after the phase alignment and summation. The beam data is composed of a plurality of echo data items arranged in the depth direction corresponding to the received beams. A plurality of beam data items obtained by single electronic scanning form received frame data.

A transmission/reception controller 44, based on transmission/reception control data transmitted from the BE device, controls transmitting signal generation and received signal processing. A beam processor 50 is a circuit that applies various data processing, such as detection processing, logarithmic transformation processing, and correlation processing, to the individual beam data input thereto in a time sequence order. A control unit 52 controls the operation of the FE device 12 as a whole. The control unit 52 further executes control for transmitting the beam data sequentially fed from the beam processor 50 using wire transmission or wireless transmission. In the present embodiment, the control unit 52 also functions as a wire communication device. A wireless communication device 54 is a module for performing communication according to the first wireless communication mode, and a wireless communication device 56 is a module for performing communication according to the second wireless communication mode. Reference numeral 18 denotes a wireless communication path according to the first wireless communication mode and reference numeral 20 denotes a wireless communication path according to the second wireless communication mode. Although each of the wireless communication paths 18 and 20 is a two-way transmission path, in the present embodiment, the former is used to transmit a great amount of data from the FE device 12 to the BE device and the latter is used to transmit a control signal from the BE device to the FE device 12. Reference numeral 64 denotes a terminal for wire communication, to which a wire communication path 22 is connected. Reference numeral 66 denotes a terminal for power source, to which a power source line 26 is connected. The power source line 26 supplies direct current power from the FE device 12 to the BE device, as described above.

A battery 60 is a lithium ion battery, for example, and a power source controller (power source circuit) 58 controls charging and discharging of the battery 60. During use of the battery, electric power is supplied from the battery 60 to each circuit within the FE device 12 via the power source controller 58. The power source controller 58 includes a booster converter. Reference numeral 62 denotes a power source line when an AC adaptor is connected. When an AC adaptor is connected, external electric power is supplied to each circuit within the FE device 12 with the operation of the power source controller 58. At this time, if the charging amount of the battery 60 is less than 100%, the external power is used to charge the battery 60.

During an ultrasonic diagnostic operation (during transmission and reception), the FE device 12, in accordance with control on the BE device side, executes supply of a plurality of transmitting signals to the probe and processing of a plurality of received signals obtained thereafter in a repeated manner. A plurality of beam data items in time sequence order thus obtained are sequentially transmitted to the BE device through wireless communication in the separated state and through wire communication in the docking state. At this time, the individual beam data items are converted to a plurality of packets and transmitted according to a so-called packet transmission mode.

Known operation modes include, in addition to the B-mode, various modes including a CFM mode, an M mode, and a D mode (PW mode and CW mode), for example. Transmission and reception processing for harmonics imaging and elastic information imaging may also be executed. Circuits such as a living body signal input circuit, for example, are omitted in FIG. 1.

(3) Back-End Device

Figure 5:
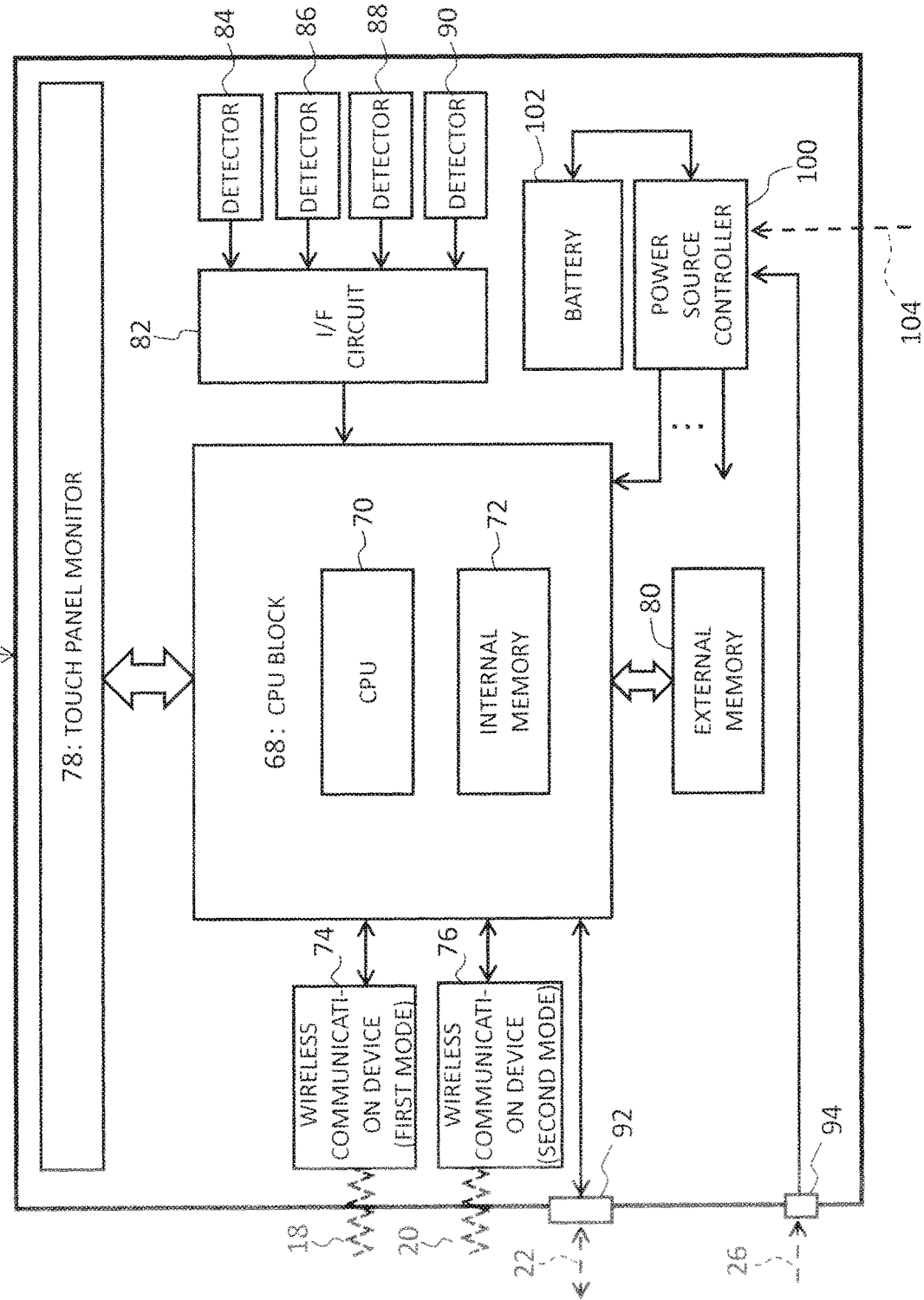
FIG. 5 is a block diagram of a back-end device.

FIG. 5 is a block diagram illustrating the BE device 14. In FIG. 5, individual blocks show hardware such as a processor, a circuit, memory, and other components. A CPU block 68 includes a CPU 70 and an internal memory 72, for example. The internal memory 72 functions as a working memory or a cache memory. An external memory 80 connected to the CPU block 68 stores an OS, various control programs, and various processing programs, for example. The various processing programs include a scan convert processing program. The external memory 80 also functions as a cine memory having a ring buffer structure. A cine memory may be formed on the internal memory 72.

The CPU block 68 performs scan convert processing with respect to a plurality of beam data items forming received frame data to thereby generate display frame data. The display frame data constitute an ultrasound image (a tomographic image, for example). This processing is repeated to generate a moving image. The CPU block 68 applies various processing for displaying an ultrasound image to the beam data or an image. The CPU block 68 also controls the operation of the BE device 14 and further controls the whole ultrasonic diagnostic system.

A touch panel monitor (display panel) 78 functions as an input device and a display device. Specifically, the touch panel monitor 78 includes a liquid display device and a touch sensor and functions as a user interface. The touch panel monitor 78 shows display images including an ultrasound image, and also shows various buttons (icons) for operation.

A wireless communication device 74 is a module for performing wireless communication according to the first wireless communication mode. A wireless communication path for this wireless communication is denoted with reference numeral 18. A wireless communication device 76 is a module for performing wireless communication according to the second wireless communication mode. A wireless communication path for this wireless communication is denoted with reference numeral 20. The CPU block 68 also has a function to perform wire communication according to the wire communication mode. In the docking state, the wire communication line is connected to a wire communication terminal 92, and the power source line 26 is connected to a power source terminal 94.

A plurality of detectors 84 to 90 are connected to the CPU block 68 via an I/F circuit 82. The detectors may include a photosensor, a proximity sensor, a temperature sensor, and other sensors. A module such as a GPS may also be connected to the CPU block 68. The I/F circuit 82 functions as a sensor controller.

A battery 102 is a lithium ceramic battery, and a power source controller (power source circuit) 100 controls charging and discharging of the battery. During operation of the battery, the power source controller 100 supplies electric power from the battery 102 to each circuit within the BE device 14. When the battery is not in operation, the power source controller 100 supplies the electric power from the FE device or the electric power from the AC adaptor to each circuit within the BE device 14. Reference numeral 104 denotes a power source line from the AC adaptor.

The BE device 14 controls the FE device and simultaneously sequentially processes the plurality of beam data items transmitted from the FE device to generate an ultrasound image, which is then displayed on the touch panel monitor 78. At this time, a graphic image for operation is also displayed with the ultrasound image. In a normal real time operation, the BE device 14 and the FE device are electrically connected with each other by wire or wirelessly, and an operation for ultrasound diagnosis is continuously executed while the operations of these devices are synchronized. In the freeze state, in the BE device 14, the operations of the transmitting signal generating circuit and the received signal generating circuit are stopped, and the operation of the booster circuit within the power source controller 100 is also stopped. The BE device displays a still image when frozen and retains the content of the still image. The BE device may be configured to be connected to an external display device.

(4) Communication Mode

FIG. 6 summarizes communication modes used in the docking state 118 and the separated state 120. Reference numeral 110 denotes the first wireless communication mode and reference numeral 112 denotes the second wireless communication mode. Reference numeral 114 denotes the wire communication mode. Reference numeral 116 denotes the content of the wireless communication modes. In the docking state 118, wire communication is selected; in the FE device and the BE device, the operations of the first wireless communication device and the second wireless communication device are stopped, and power saving is achieved. In the separated state 120, on the other hand, wireless communication is selected, and in the FE device and the BE device, the first wireless communication device and the second wireless communication device work. At this time, the operation of the wire communication system is stopped. The first wireless communication mode 110 has a higher speed than the second wireless communication mode 112. In other words, while the second wireless communication mode 112 has a lower speed than the first wireless communication mode 110, the second wireless communication mode 112 is simpler and less expensive, and consumes less power. The wire communication mode includes TCP/IP protocol on the Ethernet (registered mark). The first wireless communication mode includes IEEE802.11 and the second wireless communication mode includes IEEE802.15.1. These are only examples, and other communication modes may be used. In any case, it is desirable to use secure communication modes.

In the present embodiment, the wireless communication device in accordance with the second wireless communication mode 112 has a function to automatically vary the transmission power in accordance with the receiving intensity (that is, a distance). More specifically, the wireless communication device automatically executes control to lower the transmission power of the BE device and the FE device when the BE device is in proximity to the FE device. It is therefore possible to determine that both devices are in proximity to each other based on a change in the transmission power which is set. Alternatively, the proximity of the two devices may also be determined based on the receiving intensity, the receiving error rate, and other parameters. Further, a proximity sensor may also be used.

(5) Description of Operation

Figure 7:
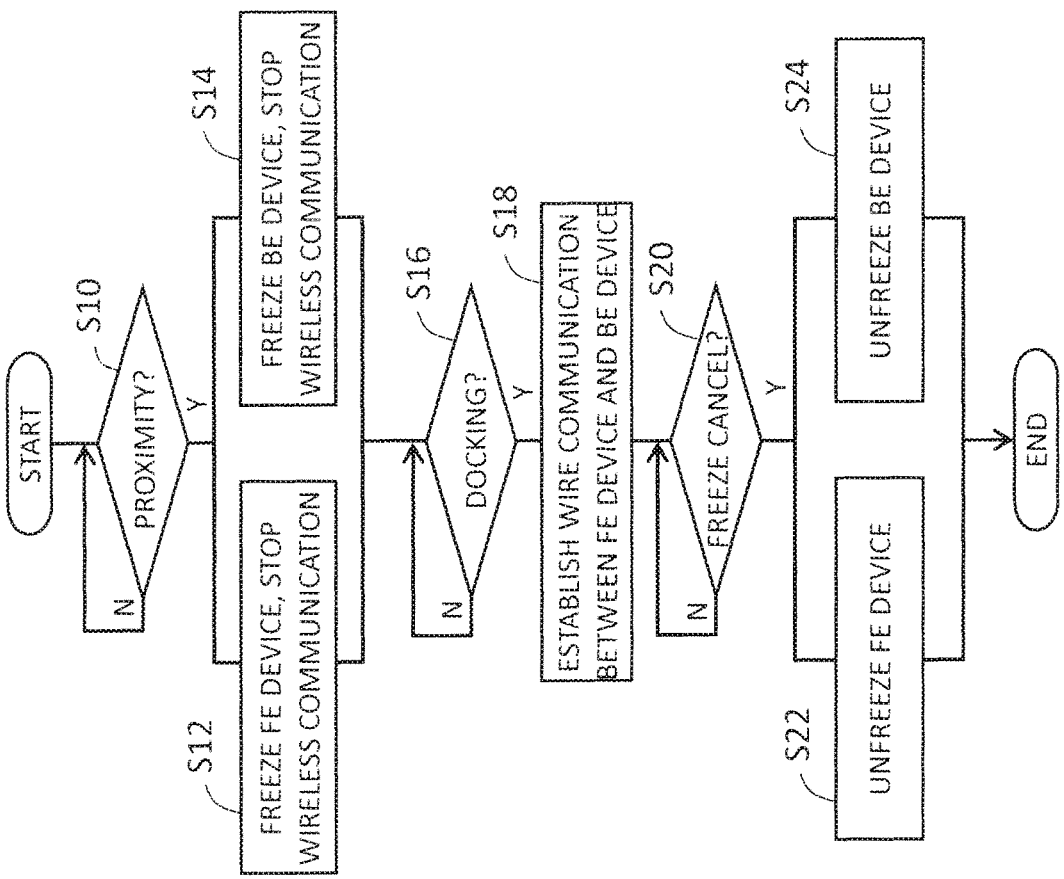
FIG. 7 is a flowchart illustrating an example operation executed immediately before docking.

FIG. 7 illustrates an example basic operation performed in the course of a shift from the separated state to the docking state. In step S10, immediately-before state of docking; that is, proximity, is determined. In the present embodiment, the second wireless communication device within the FE device and the second wireless communication device within the BE device each performs control for varying the transmission power based on the intensity of an electric field. In step S10, referring to the operation conditions of the respective second wireless communication devices, and more specifically, referring to the transmission power (electric power value) in a predetermined register of each wireless communication device, proximity is determined simultaneously in both devices based on a change in the transmission power. While in the present embodiment, proximity is determined simultaneously in both devices, proximity may be determined in one of the devices and the result may be transferred to the other device. In an extremely proximate state, however, as the wireless communication may not be performed correctly due to saturation of the receive signals, it is reliable that proximity is determined individually in the FE device and the BE device.

Steps S12 and S14 are executed in parallel. In step S12, the FE device is placed in a freeze state, and simultaneously the wireless communication is stopped. The freeze state is an operation limited state or a partially non-operating state. Specifically, the operations of the transmitting circuit and the booster circuit (booster converter) are stopped. The interruption control for the wireless communication results in stop of the operation of the two wireless communication devices within the FE device. This interruption control reduces a waste of power, leading to power saving. In step S12, other control for establishing the freeze state is executed, as required. At this time, operations necessary for the future docking state (e.g., wire communication) may be prepared. In step S14, on the other hand, the BE device is placed in the freeze state, and simultaneously, the wireless communication is stopped. Specifically, upon freeze of the BE device, storage of a new image in a cine memory and further image processing are stopped. As a result, an image displayed at the time of freeze remains as a still image until an examiner performs any operation or input. Upon the freeze, the operations of the two wireless communication devices within the BE device are also stopped, which achieves power saving. In step S14, other control for establishing the freeze state is executed as required. Further, operations necessary for the future docking state (e.g., wire communication) may be prepared, as required.

In step S16, whether or not the docking state is established is determined. The docking state is individually determined in each device by detecting connection of the connectors in each device, for example. After establishment of the docking state, in step S18, the wire communication is automatically established between the FE device and the BE device. These devices are already paired, and therefore the wire communication is automatically established without input for authentication being requested. In other words, mutual device authentication is automatically completed. However, certain user authentication may be performed at this time. Also, an operation for unfreezing may be awaited to establish the wire communication.

After step S18 or in parallel to step S18, in step S20, whether or not the examiner has performed an operation for unfreezing is determined. If yes, in steps S22 and S24, the freeze states of the FE device and the BE device are cancelled. In other words, these devices return to a normal real-time operation state. Steps S22 and S24 are executed in parallel. Specifically, in step S22, transmission of ultrasound waves is resumed in the FE device. In other words, the operations of the booster circuit and the transmitting circuit are resumed. In addition, control operations necessary in association with the unfreezing are executed. In step S24, scan convert processing, storage of an image in the cine memory, processing of an image read from the cine memory, and other processing operations are resumed in the BE device, and display of a moving image is also resumed accordingly. In addition, control operations necessary in association with the unfreezing are executed.

When the FE device and the BE device are connected by wire, wireless communication is not performed between these devices. In other words, the respective wireless communication devices are placed in a non-operating state, resulting in power consumption. Once input of unfreezing is enabled, a message to encourage such input is displayed on the display screen of the BE device. The icons displayed on the display screen include an icon for unfreezing.

As described above, according to the present embodiment, in the course of a shift from the separated state to the docking state, prior to docking, more specifically, immediately before docking, proximity between the FE device and the BE device is determined as a spatial relationship between these devices. Using this determination as a trigger, each device then automatically transitions to the freeze state. This mechanism can be used to prevent problems caused by wireless communication errors occurring in the proximity state, problems of the system operation being unstable due to the change in the state, and other problems. Further, stop of the operation of the booster circuit (booster converter) at the time of proximity increases safety. In general, the examiner, when wishing for a docking state, is not executing an ultrasonic test itself with respect to the examinee even if transmission and reception of ultrasound waves is actually performed. Therefore, the examiner would not feel that the above-described control is burdensome or inconvenient. The examiner would rather feel convenience because an operation for freezing can be omitted.

If the freeze state has been already established between the two devices before determination of proximity, the freeze state would be maintained when determining proximity. Even in this case, at the time of proximity determination, wireless communication is stopped and other necessary control operations are executed.

Figure 8:
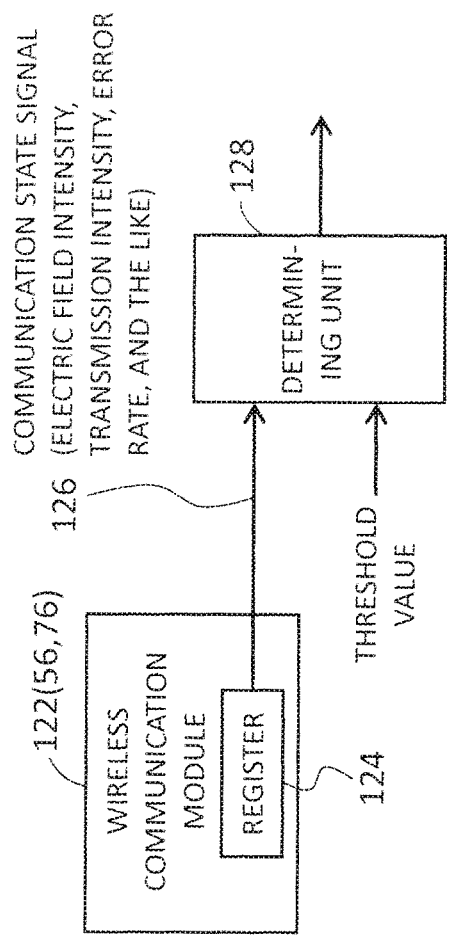
FIG. 8 is a diagram showing a first example proximity decision.

FIG. 8 illustrates a first example proximity determining method. A second wireless communication module 122 (wireless communication devices 56 and 76) in the FE device and the BE device has a function to detect the intensity of an electric field, a function to automatically reduce the transmission power in accordance with an increase in the intensity of the electric field, a function to detect an error rate, and other functions. A register 124 stores therein status data indicating communication states such as the intensity of a received electric field, the transmission power, and the error rate. A determining unit 128 refers to the data stored in the register 124 as a communication state signal 126, and determines proximity based on the communication state signal 126. A method for determining proximity can be selectively adopted from among a method for determining proximity when the transmission power is equal to or less than a threshold value, a method for determining proximity when the intensity of a receive electric field is equal to or greater than a threshold value, a method for determining proximity when the error rate is equal to or greater than a threshold value, and other methods, for example. In preferred embodiments, each of the FE device and the BE device individually determines proximity. The determining unit 128 is implemented as a function of the control unit, for example, in the FE device and is implemented as a function of the CPU block, for example, in the BE device.

Figure 9:
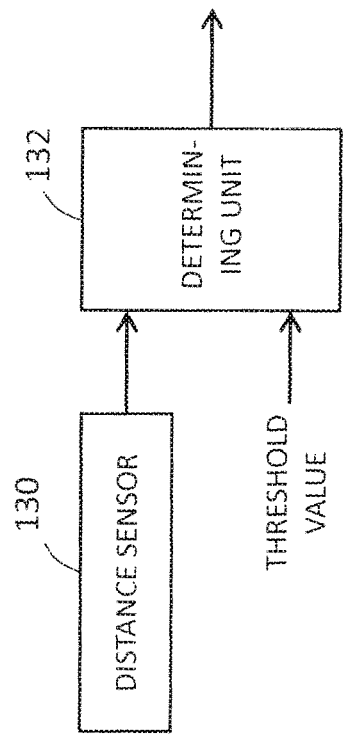
FIG. 9 is a diagram showing a second example proximity decision.

FIG. 9 illustrates a second example proximity determining method. Each of the FE device and the BE device includes a distance sensor 130 which detects a distance between the devices. The distance sensor is disposed close to a docking connector, for example. When an output signal from the distance sensor 130 is equal to or less than a predetermined value (when the distance between the devices is equal or less than a fixed value), a determining unit 132 determines proximity. Similar to the first example described above, the determining unit 132 is implemented as a function of the control unit, for example, in the FE device and is implemented as a function of the CPU block, for example, in the BE device. An optical sensor, an ultrasonic sensor, a magnetic sensor, and other sensors may be used as the distance sensor 130.

Figure 10:
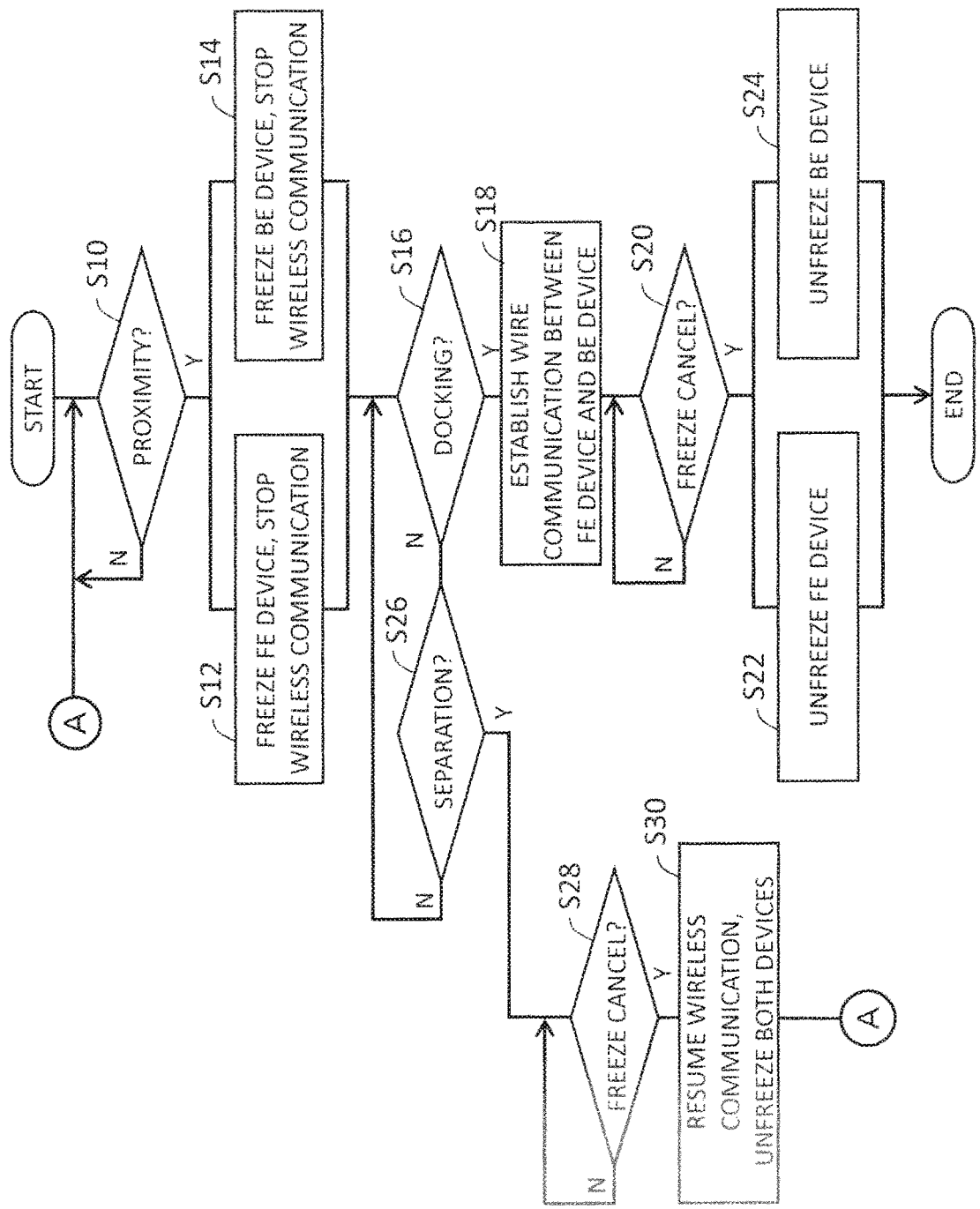
FIG. 10 is a flowchart illustrating another example operation executed immediately before docking.

FIG. 10 illustrates another example operation performed in the course of a shift from the separated state to the docking state. In FIG. 10, steps similar to those shown in FIG. 7 are designated by corresponding reference numerals and will not be described. In the basic operation example shown in FIG. 7, a situation in which the FE device and the BE device are relatively withdrawn from each other (a situation in which proximity is cancelled) after the proximity is determined but before the docking is determined. However, in the example operation illustrated in FIG. 10, such a situation is fully considered.

In step S26 in FIG. 10, when, prior to the docking determination, separation is determined; that is, when cancellation of the proximity state is determined, whether or not the examiner has performed an unfreezing operation is determined in step S28. If yes is determined, in step S30, wireless communication is automatically established between the FE device and the BE device, and wireless communication is resumed. Thereafter or simultaneously, the freeze state is cancelled in both devices, and a normal operation state is placed. Then, the process returns to step S10. If, in step S28, the proximity state is determined once again before the unfreezing operation is determined, the processes in step S10 and the subsequent steps are to be executed. To perform the control operation illustrated in FIG. 10, the proximity determining method based on a result of detection of the distance between the devices, rather than the proximity determining method based on a change in the wireless communication state, is preferably used.

Figure 11:
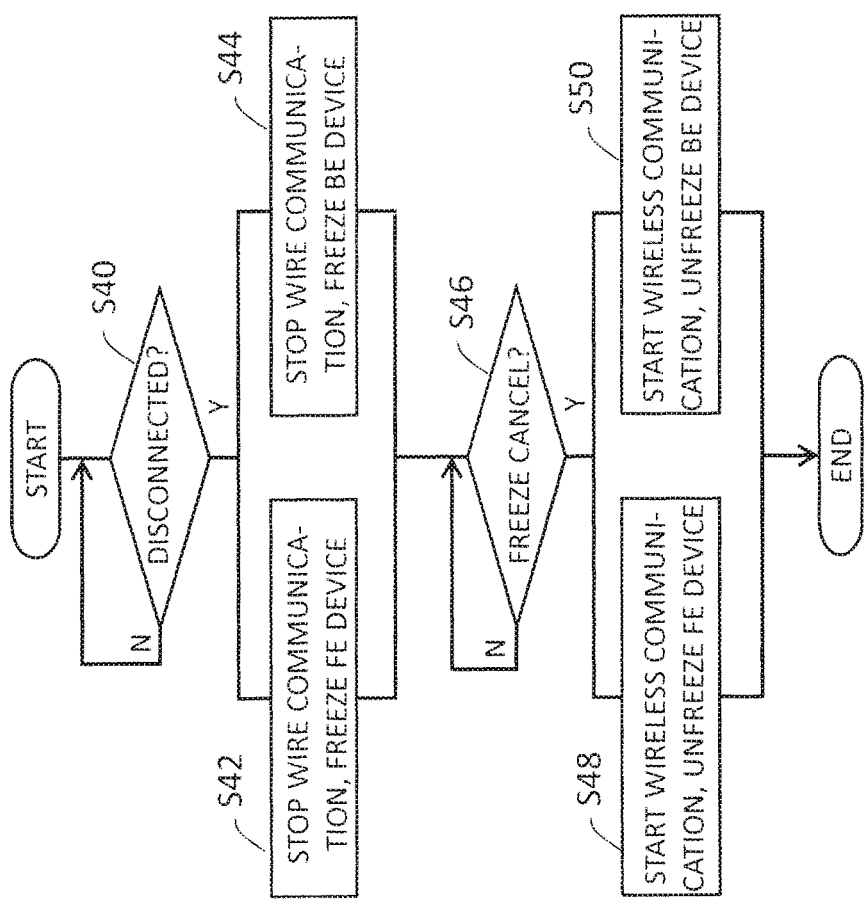
FIG. 11 is a flowchart illustrating a first example operation when the separated state is established.

FIG. 11 illustrates an example operation performed when shifting from the docking state to the separated state. In step S40, disconnection (separated state) is determined. Disconnection is determined based on physical and electrical separation between the connector of the FE device and the connector of the BE device. Based on this determination, in steps S42 and S44, wire communication is stopped in the FE device and the BE device, and simultaneously, these devices are placed in a freeze state. In step S46, whether or not an unfreezing operation has been performed is determined, and if the unfreezing operation is confirmed, in steps S48 and S50, wireless communication is established between the two devices, so that wireless communication is resumed. Thereafter or simultaneously, the freeze state is cancelled in the FE device and the BE device, and the normal real-time operation state is resumed.

With the example operation illustrated in FIG. 11, while it is not possible to detect a separated state in advance to prepare for a change of state, it is possible to detect disconnection to reliably place the individual devices in a freeze state. As, in general, an ultrasonic test is not actually being performed with respect to an examinee during such transition, no special problems would arise by automatically establishing the freeze state. Rather, this mechanism is convenient and safe for a user. Alternatively, the processes in steps S42 and S44 may be executed prior to formation of the separated state, by using, as a trigger, an output from a sensor disposed for detecting immediately-before separation.

Figure 12:
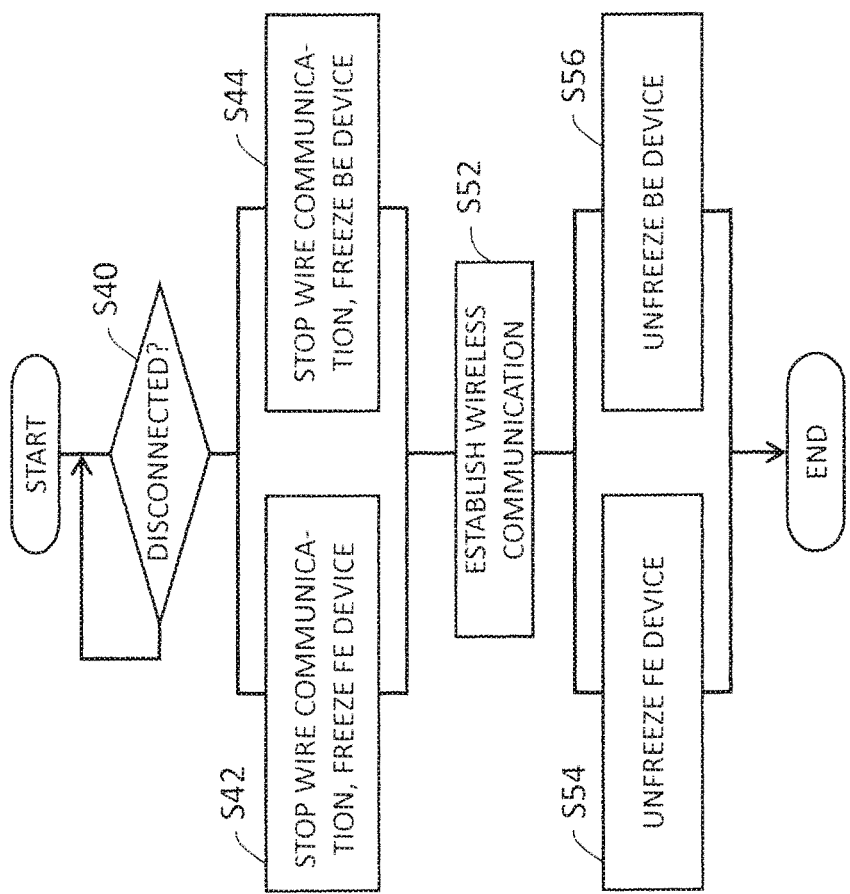
FIG. 12 is a flowchart illustrating a second example operation when the separated state is established.

FIG. 12 illustrates another example operation performed when shifting from the docking state to the separated state. In FIG. 12, the process steps similar to those illustrated in FIG. 11 are designated by the corresponding reference numerals and will not be described. In this example operation, after both devices are placed in the freeze state, in step S52, wireless communication is automatically established. In preferred embodiments, the process in step S52 is executed upon detection of separation of the devices from each other by a predetermined distance, for example. Alternatively, establishment of wireless communication may be started from immediately after disconnection. After establishment of wireless communication, in steps S54 and S56, the freeze state is cancelled in the both devices. In other words, after disconnection, the devices are automatically return to the normal operation state. This control process eliminates the need for an unfreezing operation by the examiner. However, as it is sometimes more appropriate to cause the devices to return to the normal operation state after confirmation by the examiner, the system may be configured to enable the examiner to preset a desired method from among manual return and automatic return.

In an ultrasonic diagnostic system formed of a portable FE device and a portable BE device, in accordance with a diagnosis situation and other status, there can occur a transition of state from the separated state to the docking state and a transition of state from the docking state to the separated state. In such a transition of state, the operation according to the above embodiment can avoid problems such as examiner's confusion and unstable system operation, thereby providing an ultrasonic diagnostic system with good usability.

(6) Other Configurations

Figure 13:
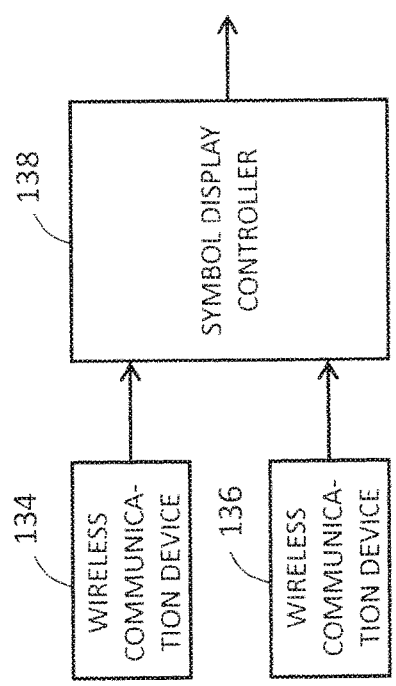
FIG. 13 is a block diagram for explaining symbol display processing.
Figure 14:
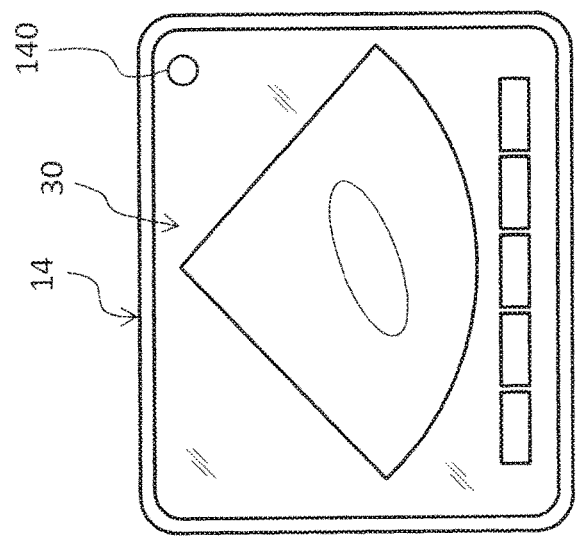
FIG. 14 is a diagram illustrating example display of a symbol.

According to the present embodiment, in the separated state, the FE device and the BE device are connected with each other with two types of wireless communication paths. The system cannot operate until both of these two types of wireless communications are established. Therefore, when displaying the wireless state, it is preferable, from a viewpoint of whether or not the system operation is available, to display the wireless state with AND conditions, rather than to display the states of the two types of wireless communication individually. As illustrated in FIG. 13, for example, it is preferable to cause a symbol display controller 138 receiving two wireless state signals from the two wireless communication devices to display a symbol indicating that the wireless state is OK only when both of the two wireless state signals show that communication is available. An example is shown in FIG. 14. Specifically, the display panel 30 of the BE device 14 shows a symbol 140 indicating a wireless state near an ultrasound image. This symbol 140 is displayed only when both of the two types of wireless communications are established and is not displayed when at least one of the wireless communications is not established. While the symbol 140 which can indicate the magnitude of the electric field may be displayed, in the present system, as the examiner is interested in whether or not the system can operate, the symbol is displayed to indicate that wireless communication is available (OK) without using such a stepwise indication. However, other display modes may be adopted.

FIG. 15 illustrates another embodiment. An ultrasonic diagnostic system includes an FE device 142, a BE device 144, and a probe 146. In the illustrated example, the FE device 142 and the BE device 144 are connected with each other by two types of wireless communications (see reference numeral 148). The probe 146 and the FE device 142 are connected with each other through wireless communication 150. In this case, two types of wireless communications may be used. When this configuration is adopted, as the probe 146, a wireless probe including a transmitting and receiving circuit is used. The probe 146 and the FE device 142 may be configured to be connected through a cable (electrical docking), in addition to wireless connection. In this case, the technique described in the above embodiment may be applied between the probe 146 and the FE device 142.

The invention claimed is:

1. An ultrasonic diagnostic system, comprising:
a first device configured to perform ultrasonic diagnosis;
a second device configured to perform, with the first device, the ultrasonic diagnosis; and
in a separated state in which the first device and the second device are separated from each other, the first device and the second device communicating with each other according to a wireless communication mode, in a docking state in which the first device and the second device are coupled to each other, the first device and the second device communicating with each other according to a wire communication mode,
an immediately-before-docking state determining unit configured to determine an immediately-before state of docking during a course of a change of state from the separated state to the docking state,
the first device comprising a first controller configured to cause an operation state of the first device to transition from a normal operation state to an operation limited state when the immediately-before state of docking is determined,
the second device comprising a second controller configured to cause an operation state of the second device to transition from a normal operation state to an operation limited state when the immediately-before state of docking is determined.

2. The ultrasonic diagnostic system according to claim 1, wherein
the first device comprises a transmitting circuit, and
the first controller is configured to stop operation of the transmitting circuit at the time of transition to the operation limited state.

3. The ultrasonic diagnostic system according to claim 2, wherein
the first device comprises a power source circuit including a booster converter, and
the first controller is configured to stop operation of the booster converter at the time of transition to the operation limited state.

4. The ultrasonic diagnostic system according to claim 1, wherein
the second controller is configured to change moving image display to still image display at the time of transition to the operation limited state.

5. The ultrasonic diagnostic system according to claim 1, wherein,
the immediately-before state determining unit is configured to determine the immediately-before of docking when the first device and the second device are in a proximity relationship.

6. The ultrasonic diagnostic system according to claim 5, wherein
the immediately-before state determining unit is configured to determine the immediately-before state of docking based on a wireless communication state between the first device and the second device.

7. The ultrasonic diagnostic system according to claim 6, wherein
the immediately-before state determining unit comprises:
a first immediately-before state determining unit disposed in the first device, the first immediately-before state determining unit being configured to determine the immediately-before state of docking based on the wireless communication state; and a second immediately-before state determining unit disposed in the second device, the second immediately-before state determining unit being configured to determine the immediately-before state of docking based on the wireless communication state, the first controller is configured to cause the operation state of the first device to transition to the operation limited state when the first immediately-before state determining unit determines the immediately-before state of docking, and the second controller is configured to cause the operation state of the second device to transition to the operation limited state when the second immediately-before state determining unit determines the immediately-before state of docking.

8. The ultrasonic diagnostic system according to claim 1, wherein
the first controller and the second controller are configured to resume communication using the wire communication mode after transition to the operation limited state and formation of the docking state.

9. The ultrasonic diagnostic system according to claim 1, further comprising:
a separation determining unit configured to determine a change of state from the docking state to the separated state as separation,
wherein
the first controller is configured to cause the operation state of the first device to transition from the normal operation state to the operation limited state when the separation is determined, and
the second controller is configured to cause the operation state of the second device to transition from the normal operation state to the operation limited state when the separation is determined.

10. The ultrasonic diagnostic system according to claim 1, wherein
the first device and the second device are configured to communicate with each other using a first wireless communication mode and a second wireless communication mode in the separated state.

11. The ultrasonic diagnostic system according to claim 10, wherein
the first wireless communication mode is a higher speed mode than the second wireless communication mode,
the first device is a front-end device including a transmitting circuit and a receiving circuit,
the second device is a back-end device including an input device and a display device,
the first wireless communication mode is used to transmit data from the front-end device to the back-end device, and
the second wireless communication mode is used to transmit a control signal from the back-end device to the front-end device.

12. The ultrasonic diagnostic system according to claim 11, wherein
the display device is configured to display a single communication establishment symbol when communication is established using both the first wireless communication mode and the second wireless communication mode, and
the communication establishment symbol is not displayed when communication is established using one of the first wireless communication mode and the second wireless communication mode and when neither the first wireless communication mode nor the second wireless communication mode establishes communication.

13. A method of controlling an ultrasonic diagnostic system comprising a first device and a second device, the first device and the second device configured to communicate with each other through a wireless communication mode in a separated state in which the first device and the second device are separated from each other, the first device and the second device configured to communicate with each other through a wire communication mode in a docking state in which the first device and the second device are coupled with each other, the method comprising:
determining an immediately-before-docking state of docking during a course of a change of state from the separated state to the docking state; and
when the immediately-before state of docking is determined, causing operation states of the first device and the second device to transition to a freeze state.

* * * * *